(12) United States Patent
Caldow et al.

(10) Patent No.: US 9,222,859 B2
(45) Date of Patent: Dec. 29, 2015

(54) APPARATUS AND METHOD FOR IMPROVING PARTICLE COUNT ACCURACY IN LOW PRESSURE APPLICATIONS

(75) Inventors: Robert Caldow, Roseville, MN (US); Steven William Kerrigan, St. Anthony Village, MN (US); Jason Paul Johnson, St. Paul, MN (US); Jacob Hackbarth Scheckman, Minneapolis, MN (US)

(73) Assignee: TSI, INCORPORATED, St. Paul, MN (US)

( * ) Notice: Subject to any disclaimer, the term of this patent is extended or adjusted under 35 U.S.C. 154(b) by 87 days.

(21) Appl. No.: 14/111,603

(22) PCT Filed: Apr. 12, 2012

(86) PCT No.: PCT/US2012/033334
§ 371 (c)(1),
(2), (4) Date: Mar. 17, 2014

(87) PCT Pub. No.: WO2012/142297
PCT Pub. Date: Oct. 18, 2012

(65) Prior Publication Data
US 2015/0160105 A1    Jun. 11, 2015

Related U.S. Application Data

(60) Provisional application No. 61/474,822, filed on Apr. 13, 2011.

(51) Int. Cl.
*G01N 1/10* (2006.01)
*G01N 1/40* (2006.01)
*G01N 15/06* (2006.01)

(52) U.S. Cl.
CPC ............... *G01N 1/40* (2013.01); *G01N 15/065* (2013.01)

(58) Field of Classification Search
CPC ... G01N 21/05; G01N 21/03; G01N 21/0303; G01N 30/74; G01N 21/031
USPC .......................................................... 356/246
See application file for complete search history.

(56) References Cited

U.S. PATENT DOCUMENTS

| | | | |
|---|---|---|---|
| 5,118,959 A | 6/1992 | Caldow et al. | |
| 5,872,622 A | 2/1999 | Schildmeyer et al. | |
| 6,388,746 B1 * | 5/2002 | Eriksson et al. | 356/318 |
| 6,980,284 B2 | 12/2005 | Ahn et al. | |
| 7,430,046 B2 * | 9/2008 | Jiang et al. | 356/336 |
| 2009/0009757 A1 * | 1/2009 | Mototsu et al. | 356/246 |
| 2011/0056273 A1 | 3/2011 | Gorbunov et al. | |

* cited by examiner

*Primary Examiner* — Tarifur Chowdhury
*Assistant Examiner* — Md Rahman
(74) *Attorney, Agent, or Firm* — Kagan Binder, PLLC (57) ABSTRACT

A saturator block assembly that is adapted for use with a condensation particle counter is described. The saturator block assembly is comprised of a member that is at least partially formed from a porous material that is adapted to absorb a working fluid. The saturator block assembly also includes at least one open column formed through the porous member. The open column is parallel with a length of the member and is adapted to emit the working fluid in vapor form from the porous material. The saturator block assembly is further comprised of an outer surface, and is adapted to operate at low pressure or low pressure transient applications. A volume of the porous material is configured so as to reduce the amount of air capable of being trapped in the pores of the porous material during low pressure or low pressure transient applications.

17 Claims, 7 Drawing Sheets

APPARATUS AND METHOD FOR IMPROVING PARTICLE COUNT ACCURACY IN LOW PRESSURE APPLICATIONS

PRIORITY CLAIM

This application claims priority to International Application No. PCT/US2012/033334, filed on Apr. 12, 2012, which in turn claims the benefit of U.S. Provisional Patent Application No. 61/474,822, filed Apr. 13, 2011, which applications are incorporated herein by reference in their entireties.

FIELD OF THE INVENTION

The invention relates generally to an apparatus and system for improving the particle count accuracy of a condensation particle counter operating with a differential inlet pressure below ambient pressure.

BACKGROUND

For many years, condensation particle counters (CPC) have been used in various settings to detect and count submicrometer particles (or other suspended aerosol elements). Condensation particle counters operate by "growing" the particles into larger droplets by condensing onto the particles a working fluid vapor. Typically, room air (or other gas(es) being monitored) is/are drawn through an inlet area into a chamber located inside a saturator block. A working fluid evaporates into a gas stream being tested or measured, saturating the stream with working fluid vapor. From the saturator, the test gas is drawn into a condenser tube and cooled sufficiently to supersaturate the vapor. Vapor condenses onto the particles, forming aerosol droplets much larger than the particles. From the condenser, the gas stream containing the grown particles or droplets passes an optical detector that senses the aerosol droplets traveling through a viewing volume defined by a laser and associated optics. For further information regarding this type of instrument, reference is made to U.S. Pat. No. 4,790,650 (Keady), U.S. Pat. No. 5,118,959 (Caldow et al.), and U.S. Pat. No. 7,407,531 (Flagan et al.), all of which are incorporated herein by reference.

The saturator block of a CPC can include at least in part a saturator block or wick that is made of a material with a certain porosity. When the bottom of the saturator block is set in a pool of working fluid at ambient pressure, the liquid is drawn or wicks up into the porous material and fills the pores. However, at equilibrium the working fluid may not fill every pore and some pores may remain filled with air.

When a CPC experiences a change in differential inlet pressure below ambient pressure, air in the pores may expand and push the working fluid out of the wick. The working fluid that has been pushed out can drain down the surface of the saturated wick in a thin film, and if not reabsorbed into the wick, can reach the saturator base and drip into the inlet of the CPC. When enough working fluid accumulates in the inlet, the sample air flow is forced to bubble through the liquid in the inlet, which in turn generates high concentrations of working fluid particles that are detected upstream in the CPC optics, leading to false counts.

There exists a need therefore for an apparatus and/or system for preventing CPC working fluid from being pushed out of the wick and/or for preventing working fluid that is pushed out of the wick from accumulating in the inlet area of the CPC to an amount where it may be aerosolized and detected as "false counts" by the CPC optics.

SUMMARY

In one example embodiment, a saturator block assembly is provided that is adapted for use with a condensation particle counter. The saturator block assembly is comprised of a member that is at least partially formed from a porous material that is adapted to absorb a working fluid. The saturator block assembly also includes at least one open column formed through the porous member. The open column is parallel with a length of the member and is adapted to emit the working fluid in vapor form from the porous material. The saturator block assembly has an outer surface and is comprised of a volume of the porous material that is configured so as to reduce the amount of air capable of being trapped in the pores of the porous material during low pressure or low pressure transient applications.

In another example embodiment, a system for improving particle count detection accuracy in a low pressure or low pressure transient application is provided that includes a condensation particle counter apparatus and a working fluid reservoir. The system comprises a saturator block assembly that includes a wick body that is configured at least partially from a porous material that is adapted to absorb a working fluid. The wick body has an outer surface and an open column formed in it that is parallel with a wick body length. A volume of porous material is configured so as to reduce the amount of air capable of being trapped in the pores of the porous material during low pressure or low pressure transient operation. The system also includes at least one channel, which is configured to direct excess working fluid away from either the at least one open column or an inlet area of the condensation particle counter, and a base that is secured to the wick body.

In still another example embodiment, a component is provided for improving particle count accuracy in a low pressure or low pressure transient application of a condensation particle counter device having a working fluid reservoir. The component comprises a cylindrical wick member that is formed from a select amount of porous material that is adapted to absorb a working fluid. The wick member is configured to absorb the working fluid to at or near the saturation point. The component also includes an outer surface and a plurality of through holes that are located within the porous material. The porous material that comprises the plurality of through holes has a pore size that is larger than the pore size of the wick member porous material and has a pore size that allows a predetermined flow of a working fluid vapor. The wick member porous material pore size is configured to prevent excess air from becoming trapped in the wick member porous material.

DETAILED DESCRIPTION

Following below are more detailed descriptions of various embodiments of the invention described herein. In particular, the various embodiments disclosed herein describe a saturator block assembly that can be used with a CPC that is subjected to a differential inlet pressure below ambient pressure. The saturator block assembly can be used to improve the particle count accuracy of the CPC subjected to such differential pressure. It should be appreciated that various aspects of the subject matter introduced above and discussed in greater detail below may be implemented in any of numerous ways, as the subject matter is not limited to any particular manner of implementation. Examples of specific implementations and applications are provided primarily for illustrative purposes.

As used herein, unless specifically stated otherwise, the term "working fluid" refers to a fluid that can be for evaporation and condensation in a CPC. Common examples include, but are not limited to, butanol, isopropyl alcohol, water, and ethylene glycol.

Saturator block assemblies optimally operate in ambient pressure applications and appear to present some operating challenges when used to operate continuously and for extended periods of time at a low differential inlet pressure, or in applications with varying inlet pressures (cycling pressures), or when dealing with a vacuum. In some of these applications, operation at a low differential inlet pressure may lead to flooding—a condition generally accepted in the aerosol science community as working fluid being pulled out of the reservoir of the CPC, through the optics and out the vacuum port into the external vacuum pump. This condition can change the operating parameters of the CPC and related external equipment, and would most likely require returning the CPC to a manufacturer or other entity for cleaning, re-calibration and/or other service.

Operation of a CPC at a low differential inlet pressure may, in some cases, also lead to false counts of particles upstream at the optics. When the inlet is blocked or subjected to a low differential pressure, a small amount of working fluid may leak out of the saturator block assembly and may eventually pool in the inlet area of the instrument, thereby blocking the sample flow through the inlet and can eventually cause a large concentration of "false" working fluid particles to be detected by the CPC. Although this phenomenon generally poses no substantial threat to the optics of the instrument, it can create a relatively short period of time in which the CPC measurement of submicron particles is incorrect.

Figure 1:
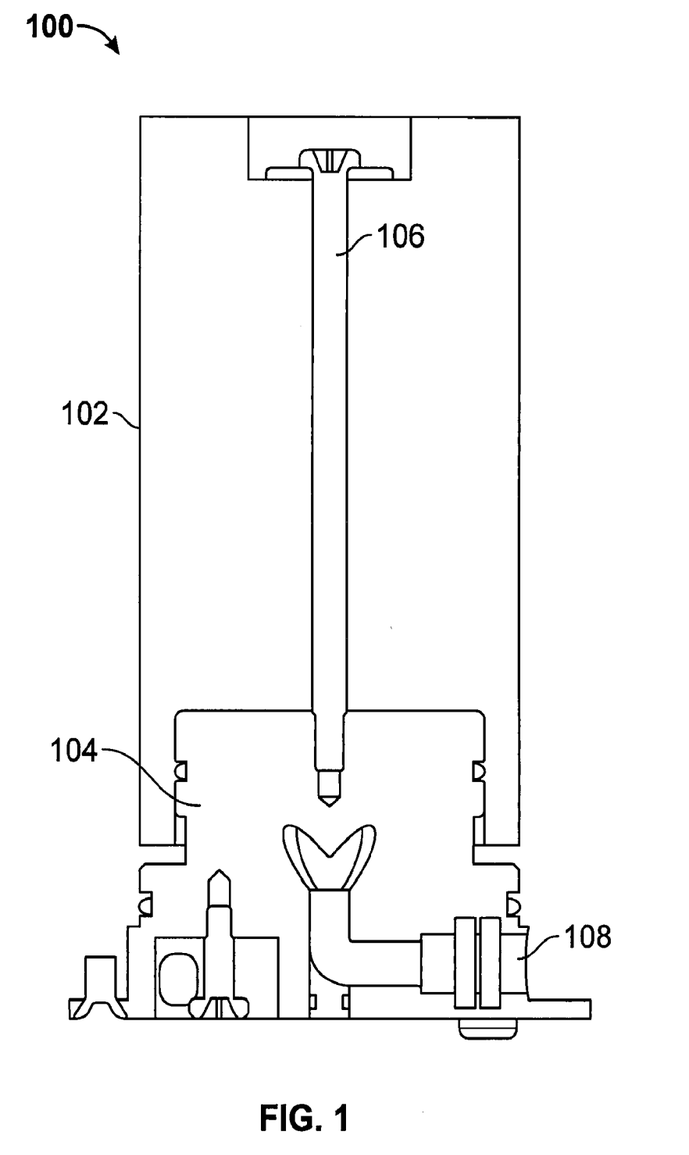
FIG. 1 is a saturator block assembly configured for use with a condensation particle counter apparatus.

It was determined that false counts during a pressure change may be related to ambient pressure air bubbles being trapped in a wick 102 of a saturator block assembly 100 as shown in FIG. 1. Wick 102 can be made of a porous material with sufficient porosity to absorb a saturating amount of a working fluid. In one example embodiment, wick 102 may be made of soft, porous, polyethylene. Referring again to FIG. 1, saturator block assembly 100 can also include a base 104 that can be secured to wick 102. In one embodiment, base 104 can be secured to wick 102 via a screw 106. As shown in FIG. 1, in one embodiment, saturator block assembly 100 can also include an inlet area 108. Room air (or other gas(es) being monitored) can be drawn through inlet area 108 into saturator block assembly 100.

When the bottom of wick 102, at ambient pressure, is set in a pool of working fluid, the liquid can wick up into the porous material and fill the pores. However, the working fluid may not fill every pore, and some pores may remain filled with air at ambient pressure.

A dry wick can experience the same process when it is installed in a CPC and the instrument is switched on at ambient pressure with, for example, a butanol bottle attached. At ambient pressure, the wick can become saturated with working fluid, but some air may remain trapped in the wick.

When the inlet pressure becomes lower than ambient pressure, any air bubbles that may have become trapped (at ambient pressure) inside the wick can expand and can either push working fluid out of the wick into the flow path of the wick, or may cause working fluid to bubble on the surface of the wick in the flow path. The bursting of these bubbles may cause working fluid to become aerosolized, which can generate a small amount of "false" particles (0-3 particles/cm$^3$) that are counted upstream by the optics. If enough working fluid is pushed out of the wick, it can drain into the inlet area of the CPC. If enough working fluid drains into and collects in the inlet area, it can block the flow path and sample air can bubble through the working fluid. This can cause a larger amount (3-100+ particles/cm$^3$) of "false" particles detected upstream by the optics.

Several empirical tests show that trapped air bubbles (at ambient pressure) can cause a working fluid accumulation problem. For example, a dry wick can be set in a pool of butanol and left for a sufficient time to absorb as much butanol as possible. If the wick is then installed in a CPC device at below ambient pressure, butanol can drip into the CPC's inlet. When this occurs, the bubbling of the butanol can be heard if a tube is attached to the inlet and extended to the observer's ear.

In another example empirical test, a wet wick 102 can be inserted into an airtight chamber filled with butanol, and a vacuum can be connected to the chamber. Initially, a large number of air bubbles can be pulled out of the wick, showing that not every pore in the wick may be filled during normal saturation of the wick at ambient pressure. If the experimental system is left at low pressure for an extended period of time, eventually no bubbles may exit the wick. This "vacuum conditioned" wick can then be removed from the chamber and installed in a CPC apparatus. Results show with this embodiment that in testing, only a small percentage of the instruments containing wicks treated this way exhibited a working fluid accumulation problem.

Figure 2A:
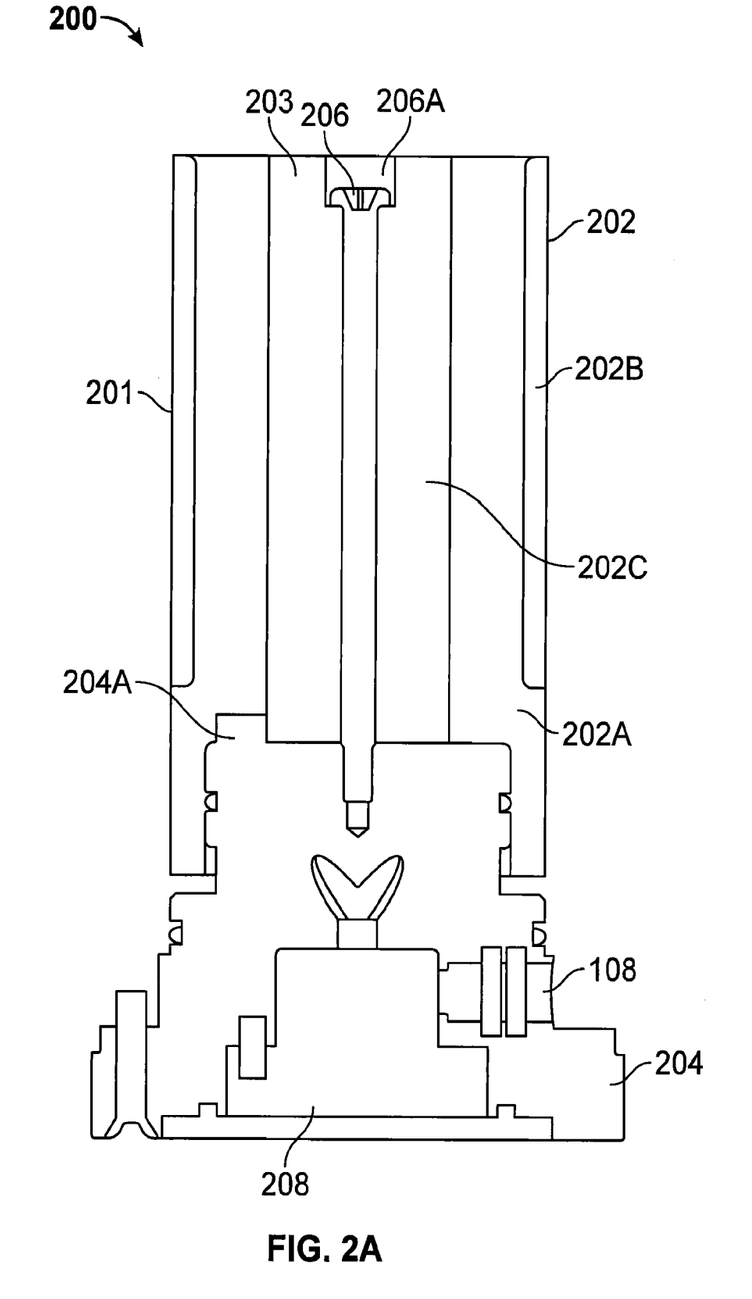
FIGS. 2A-2C illustrate example embodiments of a saturator block assembly configured for use with a condensation particle counter apparatus to prevent working fluid from draining into the inlet area.
Figure 2B:
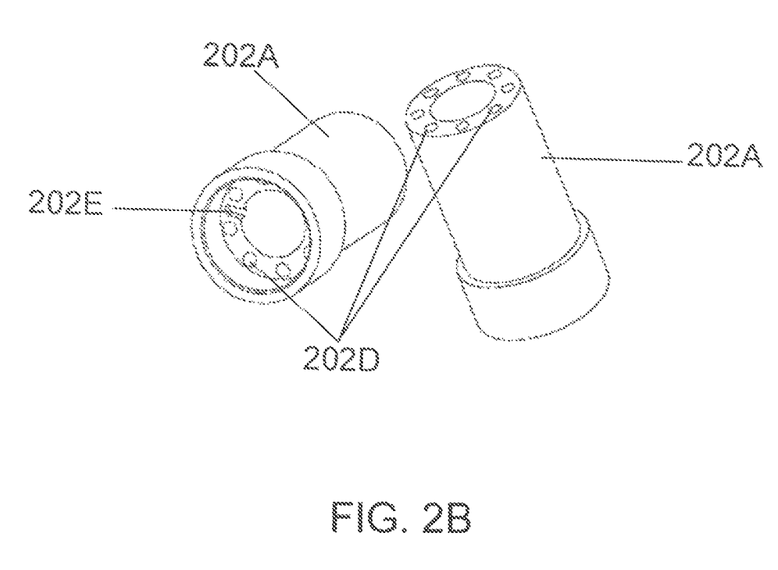
Figure 2C:
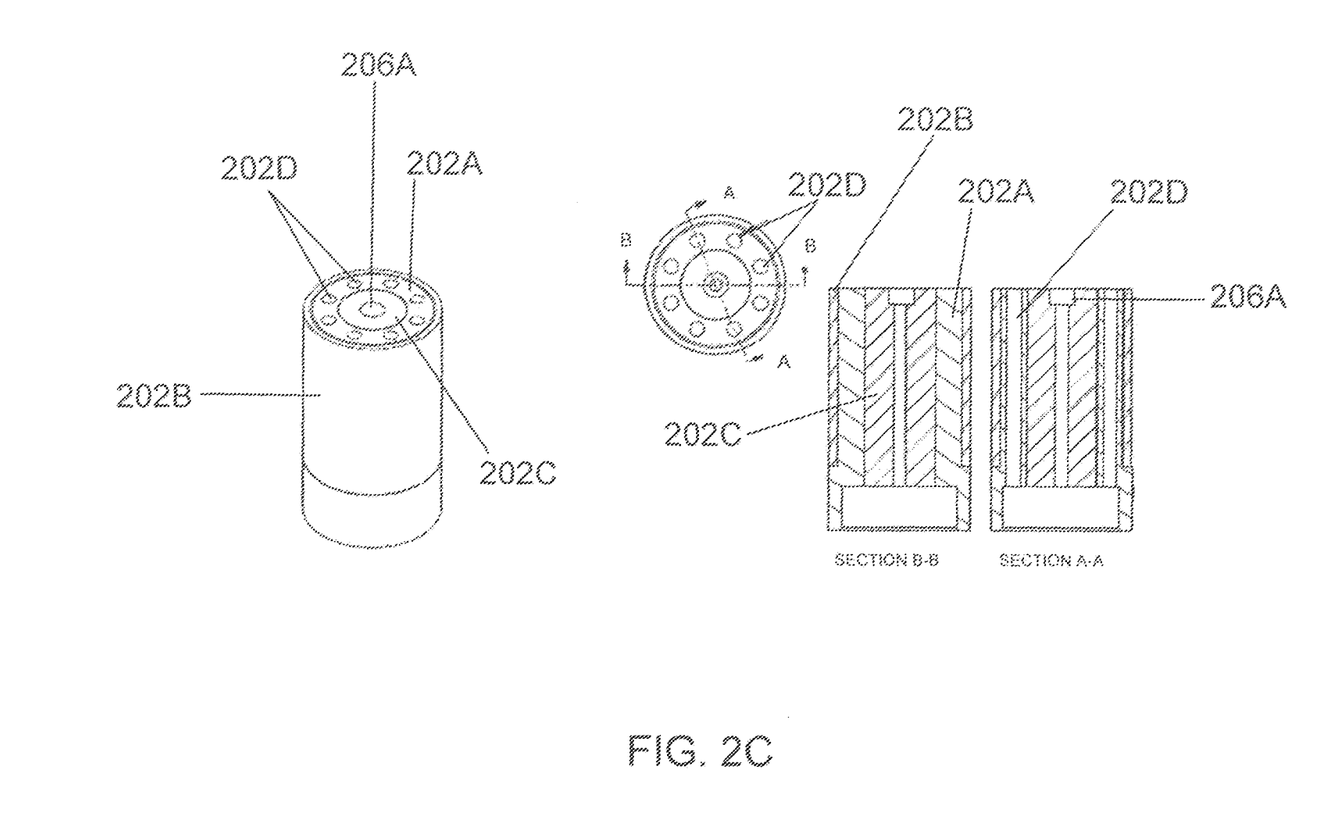

Referring now to FIGS. 2A through 2C, various example embodiments are shown of an improved saturator block assembly 200 that can be used to prevent a working fluid accumulation problem. FIG. 2A shows a saturator block assembly 200 in which the volume of porous material in wick member 202 can be minimized by a sufficient amount to reduce the amount of air capable of being trapped in the pores of the porous material during low pressure or low pressure transient applications. In one example embodiment, the volume of porous material in wick member 202 can be reduced by substituting the porous material with nonporous material in certain areas of wick member 202. In another example embodiment, the volume of porous material in wick member 202 can be reduced by substituting porous material with material that is of a different porosity in certain areas of wick member 202.

Referring to FIG. 2A, in one example embodiment, wick member 202 is shown with an outer surface 201 and a wick body 202A that can be made at least partially of a porous material that is adapted to absorb a working fluid. In one example embodiment, the porous material can be adapted to absorb working fluid at or near the saturation point of wick body 202A.

In one embodiment, the porous material can be made of soft, porous, polyethylene. In other embodiments, the porous material can include, for example, and without limitation, paper, stainless steel, ceramic, and mixtures thereof.

As shown in FIG. 2A, in one embodiment, wick member 202 can contain a hollow core 203 in which some of the wick body has been removed. In another embodiment, a plug 202C that is nonporous can be inserted into hollow core 203 of wick member 202. In an alternative embodiment, plug 202C can be made of material that is less porous than wick body 202A.

Examples of materials that can make up plug 202C include, without limitation, plastic, paper, ceramic, metal, and mixtures thereof.

As shown in FIG. 2A, in another example embodiment, some of the material around the outer surface of wick member 202 can also be removed to reduce the number of pores capable of trapping air. In place of the removed wick material, an outer sleeve 202B that is nonporous can be placed about the outer surface of wick member 202. In an alternative embodiment, outer sleeve 202B can be made of material with a porosity different than the porosity of wick body 202A.

Outer sleeve 202B can be made of, for example, and without limitation, plastic, paper, ceramic, metal and mixtures thereof.

In one embodiment, saturator block assembly 200 can further comprise a base that may be secured to wick member 202. As shown in FIG. 2A, in an example embodiment, base 204 can be held to wick member 202 via a screw 206. Other securing means known to those of ordinary skill in the art can also be used to secure base 204 to wick member 202. In the example embodiment shown in FIG. 2A, base 204 can be held to wick member 202 via a screw 206 that is placed within an aperture 206A that can run the length of wick member 202.

In another example embodiment, base 204 can also include a tab or indexing member 204A that can prevent wick member 202 from spinning or turning axially.

Referring now to FIG. 2B, in one example embodiment, wick body 202A can include one or more open columns 202D that may be parallel with wick member 202. Open columns 202D can be adapted to emit, through wick member 202, a working fluid in vapor form. In another example embodiment, columns 202D can be comprised of one or more holes that can extend from the top of wick body 202A through the entire length of wick body 202A ("through holes"). In an example embodiment shown in FIG. 2B, wick body 202A can be comprised of eight through holes that may be evenly spaced throughout wick body 202A.

In an example embodiment shown in FIG. 2B, wick body 202A can also contain a notch 202E that can mate with tab or indexing member 204A of base 204 to help prevent wick member 202 from spinning or rotating out of alignment.

FIG. 2C illustrates another example embodiment of wick member 202 in a top and bottom perspective view along with a top view and side cutaway views along lines A-A and B-B. In particular, in the embodiment shown in FIG. 2C, wick body 202A can include sleeve 202B that may be surrounded about the outer surface of wick member 202 and plug 202C that can be encased in the wick material of wick member 202. In the example embodiment shown in FIG. 2C, the top of wick member 202 can include one or more apertures (or open columns) 202D that can run the length of wick member 202 while plug 202C can include an inner aperture (or hollow core) 206A.

Referring again to FIG. 2A, in another example embodiment, saturator block assembly 200 can also include a drip guard area 208. Drip guard area 208 can be configured to capture any drops of working fluid that drip out of wick member 202 and into the inlet area of the CPC. In one example embodiment, drip guard area 208 can be comprised of a small porous cup that can be placed in the inlet area. In another example embodiment, drip guard area 208 may be comprised of a thin plate located between wick member 202 and base 204 that can aid in channeling working fluid drips back into wick member 202 and prevent any working fluid drips from falling into the inlet area. In one embodiment, the thin plate may channel working fluid back into wick member 202 to be reabsorbed by the porous material.

In an example experiment using saturator block assemblies configured according to FIGS. 2A-2C, and with a drip guard area 208, butanol dripping into the inlet area had no effect on performance.

Figure 3A:
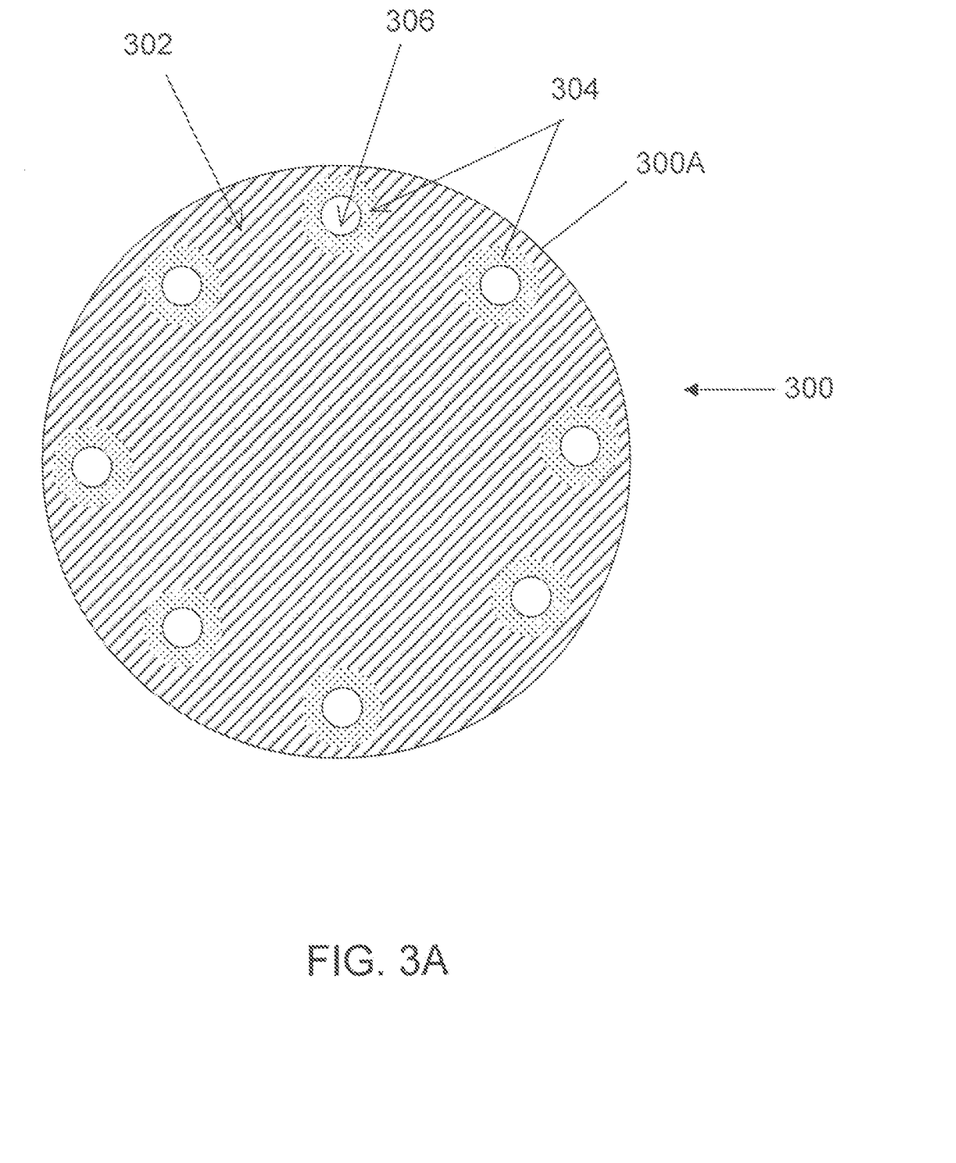
FIGS. 3A-3B illustrate example embodiments of a component that can be used with a condensation particle counter apparatus to prevent working fluid from draining into the inlet area.
Figure 3B:
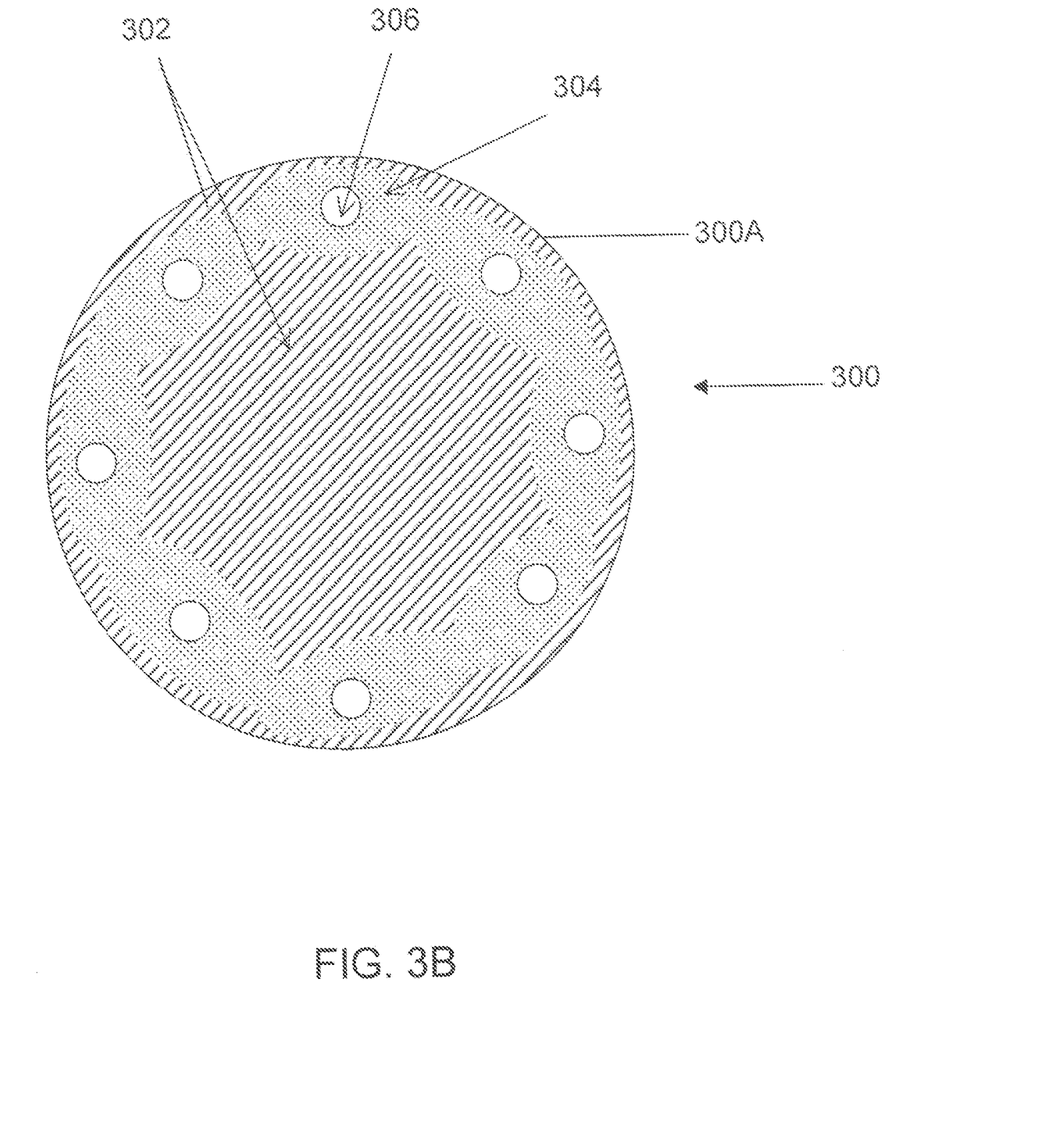

Referring now to FIGS. 3A-3B, in an alternative embodiment, cylindrical wick member 300 can be used with saturator block assembly 200 to reduce the working fluid accumulation problem. The volume of porous material in cylindrical wick member 300 can be minimized by a sufficient amount to reduce the amount of air capable of being trapped in the pores of the porous material during low pressure or low pressure transient applications. In one example embodiment, the volume of porous material in cylindrical wick member 300 can be reduced by substituting the porous material with nonporous material in certain areas of cylindrical wick member 300. In another example embodiment, the volume of porous material in cylindrical wick member 300 can be reduced by substituting porous material with material that is of a different porosity in certain areas of cylindrical wick member 300.

In one example embodiment, cylindrical wick member 300 has an outer surface and may be formed from a select amount of porous material containing a certain permeability. In another embodiment, cylindrical wick member 300 can be configured to absorb working fluid to at or near the saturation point of cylindrical wick member 300.

In the example embodiments shown in FIGS. 3A-3B, cylindrical wick member 300 can also include a cylindrical wick body 300A that may be comprised of a nonporous or less porous material 302 throughout, interspersed with porous or more porous material 304 in select areas. In one embodiment, cylindrical wick member 300 can also include a plurality of through holes (or open columns) 306 that can be located within porous material 304.

In one example embodiment, the porous material 304 that comprises the plurality of through holes 306 can have a pore size and/or pore distribution that is larger than the pore size and/or pore distribution of the less porous or nonporous material 302 that comprises the remainder of cylindrical wick body 300A. In another embodiment, the pore size of the material that comprises through holes 306 can be sufficiently large to allow a predetermined flow of a working fluid. As shown in FIG. 3A, in one example embodiment, the material of cylindrical wick body 300A closely surrounding through holes 306 can also be comprised of porous material 304. In still another example embodiment, as shown in FIG. 3B, the material in between through holes 306 may also be comprised of porous material 304.

In an alternative embodiment, wick member 202 and cylindrical wick member 300 may be comprised of a porous material that contains smaller pores in some portions of the wick member and large pores in other portions of the wick member so as to optimize the distribution of liquid and air throughout the wick member.

Figure 4:
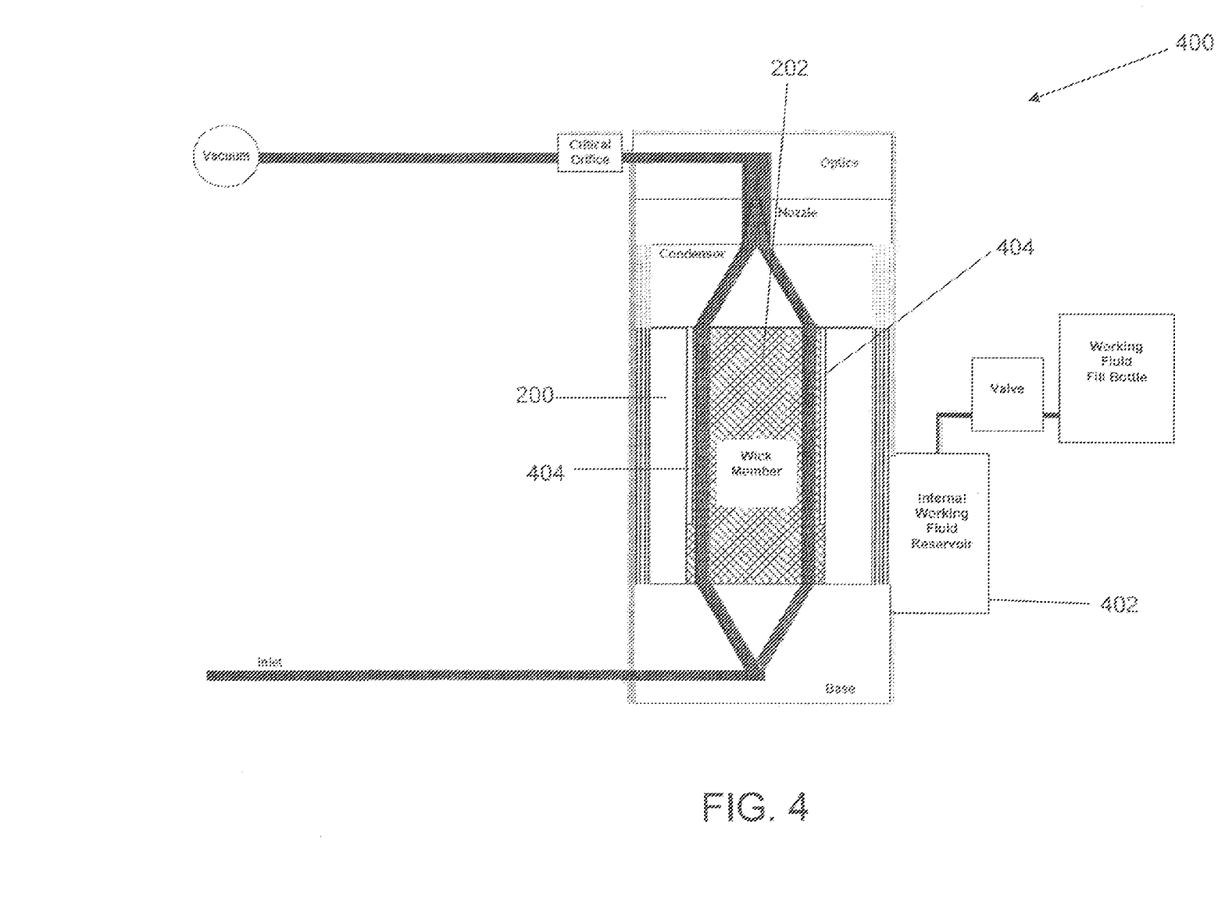
FIG. 4 illustrates an example embodiment of a system that can be used to prevent working fluid from draining into the inlet area of a condensation particle counter apparatus.

Referring now to FIG. 4, in various other embodiments of the invention, a condensation particle counter apparatus 400 is provided that can include a working fluid reservoir 402, and saturator block assembly 200. The saturator block assembly 200 can include at least one channel 404 that can be configured to direct excess working fluid away from at least one of the open columns 202D or an inlet area of the condensation particle counter. In an example embodiment, the at least one channel 404 can be located on the outer surface of wick member 202. In another example embodiment, the at least one channel 404 can be parallel with open column(s) 202D. In still another example embodiment, the at least one channel 404 can run the entire length of wick member 202, or alternatively, can run any length of wick member 202 that can allow sufficient redirection of working fluid away from open column(s) 202D or the inlet area of a CPC. The at least one channel 404 can be comprised of any material that allows redirection of excess working fluid away from open column (s) 202D or the inlet area of a CPC. In an example embodiment, the at least one channel 404 can be comprised of a porous material of sufficient porosity that can allow excess working fluid to be reabsorbed back into the porous material of wick member 202.

In various other embodiments, preventing drips of working fluid from reaching the inlet area can be accomplished by tapping at least one thread on the inside of one or more open columns 202D in order to create a spiral path which working fluid must travel down, thus increasing the surface area that the working fluid must traverse before reaching the bottom of wick member 202, and thus increasing the chances of reabsorption. Such prevention may also be accomplished by artificially sealing one or more pores in the surfaces of wick member 202 with a suitable sealant (one example, without limitation, is RTV sealant) in order to aid in channeling working fluid into the porous surfaces of wick member 202 and blocking drops of working fluid from reaching the inlet area.

In still another example embodiment, preventing drops of working fluid from reaching the inlet area can be accomplished by adding one or more inserts into one or more of open column(s) 202D, which can aid in channeling drips of working fluid back into wick member 202.

In an alternative embodiment, preventing working fluid from reaching the inlet area of a CPC can be accomplished by optimizing the pore size and/or pore size distribution of the porous material of wick member 202 in a way that can allow wick member 202 to fill with a desired level of working fluid. In another alternative embodiment, the permeability of the porous material of wick member 202 can be optimized so as to allow liquid and air to move through wick member 202 at a desired rate. In still another alternative embodiment, wick member 202 may be comprised of one or more materials of different permeability and/or different pore sizes in different parts of wick member 202.

The invention also includes methods for improving particle count accuracy in a low pressure transient application of a condensation particle counter by removing trapped air bubbles from the wick member. In one embodiment, the method can include the step of placing wick member 202 into a pool of working fluid until wick body 202A reaches its saturation point. The saturated wick member can then be placed into an airtight chamber filled with the working fluid. The wick member can be pressure-conditioned at low pressure while remaining in the airtight chamber. In one example embodiment, the step of pressure-conditioning wick member 202 can include a step of connecting a vacuum of low pressure to the airtight chamber. In one embodiment, the low pressure vacuum can remain turned on for an extended period of time. The pressure-conditioned wick member can then be removed from the airtight chamber and placed in a condensation particle counter.

In one example embodiment, the conditioned wick member can be placed in an airtight chamber filled with butanol (or similar substance) at or near the top. The vacuum can then be run from about 5 minutes to about 45 minutes.

The following patents are incorporate by reference in their entirety: U.S. Pat. Nos. 7,407,531 and 5,118,959. Having thus described several illustrative embodiments, it is to be appreciated that various alterations, modifications, and improvements will readily occur to those skilled in the art. Such alterations, modifications, and improvements are intended to be part of this disclosure, and are intended to be within the spirit and scope of this disclosure. While some examples presented herein involve specific combinations of functions or structural elements, it should be understood that those functions and elements may be combined in other ways according to the present invention to accomplish the same or different objectives. In particular, acts, elements, and features discussed in connection with one embodiment are not intended to be excluded from similar or other roles in other embodiments. Accordingly, the foregoing description and attached drawings are by way of example only, and are not intended to be limiting.

We claim:

1. A saturator block assembly adapted for use with a condensation particle counter, the saturator block assembly comprised of:
    a substantially cylindrical body member having a top end and a bottom end and an outer surface at least partially formed from a porous material adapted to absorb a working fluid from the bottom end, the cylindrical body member having a length and a longitudinal axis therethrough that is parallel with the length of the body member;
    at least one column with openings at each end, the column formed through the cylindrical body member and extending from the top end to the bottom end of the body member, the open column adapted to emit the working fluid in vapor form when the cylindrical body member length is aligned along the longitudinal axis of the cylindrical body member collinearly with a condensation particle counter chamber; and
    wherein the saturator block assembly is adapted to operate at low pressure or low pressure transient applications, and wherein a volume of the porous material is physically configured so as to reduce the amount of air capable of being trapped in the pores of the porous material during low pressure or low pressure transient applications.

2. The saturator block assembly of claim 1 further comprising at least one channel on the outer surface configured to direct excess working fluid away from at least one of the at least one open column or an inlet area of the condensation particle counter, wherein the one channel extends from the top end of the cylindrical body member towards the bottom end.

3. The saturator block assembly of claim 2 wherein the at least one channel reabsorbs the excess working fluid back into the porous material of the cylindrical body member.

4. The saturator block assembly of claim 1, wherein the cylindrical body member includes more than one open column there through that span the length of the cylindrical body member.

5. The saturator block assembly of claim 1 further comprising a nonporous outer sleeve member disposed in contact with and along the outer cylindrical surface of the cylindrical body member of the saturator block assembly.

6. The saturator block assembly of claim 1, wherein the outer surface of the cylindrical body member of the saturator block assembly further comprises an outer sleeve portion, wherein the outer sleeve portion has a porosity enabling absorption of working fluid which is different than the porosity of the porous material of the cylindrical body member of the saturator block assembly.

7. The saturator block assembly of claim 1 further comprising a hollow core formed through the cylindrical body member and parallel with the at least one open column and the axis of cylindrical body.

8. The saturator block assembly of claim 7 further comprising a nonporous plug inserted into the hollow core.

9. A system for improving particle count detection accuracy in a low pressure or low pressure transient application, the system including a condensation particle counter apparatus and a working fluid reservoir, the system comprising:
   a saturator block assembly including a wick body with a length and a longitudinal axis therethrough, a top end and a bottom end and an outer surface portion disposed about the wick body, the wick body configured at least partially from a porous material adapted to absorb a working fluid, and including an open column formed in the wick body that is parallel with the wick body length, wherein a volume of porous material is physically configured so as to reduce the amount of air capable of being trapped in the pores of the porous material of the wick body during low pressure or low pressure transient operation when the wick body member length is aligned along the longitudinal axis of the wick body collinearly with a condensation particle counter chamber;
   at least one channel configured to direct excess working fluid away from the at least one of the open column or an inlet area of the condensation particle counter; and
   a base adjacent to the wick body.

10. The system of claim 9 wherein the wick body includes more than one open column there through that span the length of the wick body.

11. The system of claim 9 wherein the at least one channel reabsorbs the excess working fluid back into the porous material of the wick body.

12. The system of claim 9 wherein the saturator block assembly is further comprised of a nonporous outer sleeve located about the outer surface of the wick body.

13. The system of claim 9 wherein the wick body is further comprised of a hollow core formed there through.

14. The system of claim 13 wherein the saturator block assembly is further comprised of a nonporous plug disposed within the hollow core.

15. The system of claim 9, further comprising an outer sleeve portion located about the outer surface of the wick body wherein the outer sleeve portion has a porosity enabling absorption of working fluid which is different than the porosity of the porous material of the wick body.

16. The system of claim 9 further comprising a drip guard area located in the inlet area of the condensation particle counter.

17. A component for improving particle count accuracy in a low pressure or low pressure transient application of a condensation particle counter device including a condensation particle counter apparatus and a working fluid reservoir, the component comprising:
   a cylindrical wick member formed from a select amount of porous material adapted to absorb a working fluid-to at or near saturation point, the wick body member having a top and bottom end and an outer surface and a longitudinal axis there through, the wick body being aligned collinearly along the longitudinal axis of the wick body with a condensation particle counter chamber; and
   a plurality of through holes located within another porous material of the wick body;
   wherein the another porous material that comprises and surrounds the plurality of through holes has a pore size that is larger than the pore size of the cylindrical wick member porous material and has a pore size that allows a predetermined flow of a working fluid vapor, the cylindrical wick member porous material pore size configured to prevent excess air from becoming trapped in the cylindrical wick member porous material.

\* \* \* \* \*